United States Patent
Trutwig et al.

(10) Patent No.: US 11,602,038 B2
(45) Date of Patent: Mar. 7, 2023

(54) PLANAR FLEXIBLE ELECTRODE ARRANGEMENT FOR A DIELECTRIC BARRIER PLASMA DISCHARGE

(71) Applicant: CINOGY GMBH, Duderstadt (DE)

(72) Inventors: Leonhard Trutwig, Duderstadt (DE); Mirko Hahnl, Berlingerode (DE); Karl-Otto Storck, Duderstadt (DE); Melanie Ricke, Katlenburg-Lindau (DE); Dirk Wandke, Heilbad Heiligenstadt (DE)

(73) Assignee: CINOGY GMBH, Duderstadt (DE)

( * ) Notice: Subject to any disclaimer, the term of this patent is extended or adjusted under 35 U.S.C. 154(b) by 586 days.

(21) Appl. No.: 16/491,629

(22) PCT Filed: Feb. 28, 2018

(86) PCT No.: PCT/DE2018/100173
§ 371 (c)(1),
(2) Date: Sep. 6, 2019

(87) PCT Pub. No.: WO2018/162003
PCT Pub. Date: Sep. 13, 2018

(65) Prior Publication Data
US 2021/0136904 A1    May 6, 2021

(30) Foreign Application Priority Data
Mar. 8, 2017    (DE) ............... 10 2017 104 852.9

(51) Int. Cl.
*H05H 1/24*    (2006.01)
*A61N 1/04*    (2006.01)

(52) U.S. Cl.
CPC ......... *H05H 1/2406* (2013.01); *A61N 1/0468* (2013.01); *A61N 1/0472* (2013.01); *H05H 1/2418* (2021.05)

(58) Field of Classification Search
CPC .. A61N 1/0468; A61N 1/0472; H05H 1/2406; H05H 1/2418
See application file for complete search history.

(56) References Cited

U.S. PATENT DOCUMENTS 7,008,596 B1 *   3/2006   Rump ..................... C01B 13/11
                                                          422/186.04
9,826,618 B2 *  11/2017   Eckert ................. A61B 18/042
(Continued)

FOREIGN PATENT DOCUMENTS

DE    20 2009 011 521 U1    2/2011
DE    10 2011 105 713 A1   12/2012
(Continued)

*Primary Examiner* — Kurtis R Bahr
(74) *Attorney, Agent, or Firm* — WCF IP

(57) ABSTRACT

A planar flexible electrode arrangement for a dielectric barrier plasma discharge has a central region (107) and an edge region (108) and at least one planar electrode (102) to which a high-voltage potential can be applied and which is embedded in a planar dielectric (101) that forms an upper face (103) and a contact face (104), wherein the planar dielectric (101), at least in the edge region (108), has the shape of a spiral-shaped wound-up strip (109) and the at least one electrode (102) is formed by at least one electrical conductor (114) that extends in the longitudinal direction of the wound-up strip (109) and that opens into an end face of the strip (109), which conductor (114) is surrounded, with the sole exception of the end face of the strip (109), by the dielectric of the strip (109) and, in the region of the end face of the strip (109), is electrically insulated from the surroundings by a cover element (116). The electrode arrangement can be adapted easily, and without tools, in its bearing surface to the size of the area of a surface that is to be treated, by virtue of the fact that material recesses (111) are present across the width of the strip (109), and that the material of the dielectric (101) and of the at least one conductor (114)

(Continued)

is chosen such that the strip (109), together with the at least one conductor (114), can be torn off across its width along the material recesses (111).

11 Claims, 7 Drawing Sheets

(56) References Cited

U.S. PATENT DOCUMENTS

| | | | |
|---|---|---|---|
| 10,265,116 B2 | 4/2019 | Stieber et al. | |
| 10,357,580 B2 * | 7/2019 | Trutwig | H01J 37/32348 |
| 2013/0064726 A1 * | 3/2013 | Morfill | A01J 7/04 |
| | | | 422/186.21 |
| 2014/0182879 A1 * | 7/2014 | Busse | H01J 37/32541 |
| | | | 29/874 |
| 2015/0157870 A1 * | 6/2015 | Kalghatgi | A61N 1/0468 |
| | | | 604/23 |
| 2016/0045246 A1 | 2/2016 | Stieber et al. | |
| 2016/0262251 A1 | 9/2016 | Jung et al. | |
| 2016/0331989 A1 * | 11/2016 | Cho | H05H 1/2406 |
| 2017/0231680 A1 * | 8/2017 | Mahrenholz | H05H 1/2406 |
| | | | 606/34 |

FOREIGN PATENT DOCUMENTS

| | | |
|---|---|---|
| DE | 10 2014 220 488 A1 | 4/2016 |
| EP | 2 723 447 B1 | 6/2012 |
| GB | 2551890 A | 1/2018 |
| KR | 10-1709167 B1 | 2/2017 |
| WO | 2012/106735 A2 | 8/2012 |

* cited by examiner

PLANAR FLEXIBLE ELECTRODE ARRANGEMENT FOR A DIELECTRIC BARRIER PLASMA DISCHARGE

The invention relates to a planar flexible electrode arrangement for a dielectric barrier plasma discharge having a central region and an edge region having at least one planar electrode to which a high-voltage potential can be applied, and which is embedded in a planar dielectric material forming a top side and a bearing side, wherein the planar dielectric material has the shape of a strip wound in a spiral at least in the edge region and the at least one electrode is formed by at least one electrical conductor, which extends in the longitudinal direction of the wound strip and discharges into an end surface of the strip, and with the exception of solely the end surface of the strip is enclosed by the dielectric material of the strip and is electrically insulated from the surroundings in the region of the end surface of the strip using a cover element.

Such a planar flexible electrode arrangement is known from EP 2 723 447 B1. The formation of the dielectric material as a strip wound in a spiral in the edge region of the electrode arrangement can be used to adapt the active contact surface of the electrode arrangement on the bearing side of the dielectric material to an underlying surface with respect to the size. For this purpose, the strip wound in a spiral can be shortened at a suitable point with the aid of a tool in order to reduce the size of the bearing surface in the desired manner. In this manner, a dielectric barrier plasma field can be generated in the required size by means of the electrode arrangement and can act, for example, on a skin surface of a human or animal body. In this case, the skin or another surface to be treated can function as a counter electrode if the surface is sufficiently conductive. For this purpose, the electrode is supplied with a high voltage, which is sufficient to generate the plasma in an air space between the electrode arrangement and the surface to be treated, in particular the skin. In order that a defined air space is established when the electrode is applied to the surface to be treated, the dielectric material can be provided on its bearing surface with a structure in the form of nubs, a grid, or the like, the top side of which is formed for bearing on the surface to be treated and forms sufficient air intermediate spaces between the bearing points, surfaces, or lines, in which the dielectric barrier plasma discharge can take place.

After the strip is cut to length, for example, using scissors, the cut edge is covered using an insulating contact element, which effectuates contact with the electrical conductor forming the electrode, for example, by means of cutting contacts.

The known electrode arrangement thus enables an adaptation of the active bearing surface of the electrode arrangement to a specific usage case but does not readily permit a compact and dimensionally-stable electrode arrangement in the usage case. A suitable tool has to be provided for cutting the strip to length.

The present invention is therefore based on the object of improving a planar flexible electrode arrangement of the known type with respect to the handling capability.

To achieve this object, a planar flexible electrode arrangement of the described type is characterized in that material recesses are provided over the width of the strip, and the material of the dielectric material and of the at least one conductor is selected so that the strip together with the at least one conductor can be torn off over its width along the material recesses.

The electrode arrangement according to the invention can thus be adapted in the area step-by-step by tearing off an end of the strip having a predetermined length along the material recesses provided over the width of the strip. In this case, the material of the conductor has to be formed so that the conductor can also be torn off along the material recesses.

The material recesses can be continuous openings through the entire thickness of the dielectric material. It is essential in this case that the wall of the openings is not interrupted by the material of the conductor, but rather has a distance from the conductor so that the risk of a flashover from the high voltage onto the surface to be treated does not exist in the region of the openings forming the material recesses. Therefore, sufficient wall material of the dielectric material has to remain between the opening and the at least one conductor. If the at least one conductor is formed by a web of a specific width within the dielectric material, it can be expedient to reduce the width of the conductor in the region of the material recesses. The possibility thus exists of implementing larger material recesses without impairing the dielectric strength and in addition improving the ability to tear off the at least one conductor in the region of the material recesses.

In other embodiments, the material recesses do not form continuous openings, but rather merely effectuate a material weakening, which ensures defined tearing off along the tear-off line formed by the material recesses. In this embodiment, a secure insulation of the electrode is to be ensured in a simpler manner.

It can be expedient if the at least one conductor extends in portions of the width of the strip not interrupted by material recesses.

The ability to tear off the at least one conductor in the region of the material recesses can be promoted in that the at least one conductor has perforation passages aligned with the material recesses of the strip in the direction of the width of the strip. The defined ability to tear off is thus ensured in particular even for a conductor which is also formed, for example, by a thin metal foil.

In one preferred embodiment of the invention, the at least one conductor consists of a plastic provided with conductive additives, however, which preferably generically corresponds to the material of the dielectric material. It is thus possible, for example, to form both the dielectric material and also the at least one conductor from a silicone, wherein the silicone is made conductive by the conductive additives for the conductor, so that the electrical conductivity required for an electrode is ensured. Due to the use of substantially corresponding matrices for the dielectric material and the conductor, the conductor can be connected to the dielectric material in a materially-joined manner, for example, in a casting method. In this manner, a stable construction of the electrode arrangement which is stable with respect to the dielectric strength can be achieved.

The strip wound in a spiral of the electrode arrangement forms strip portions which are located adjacent to one another like spiral turns. These strip portions can be sufficiently dimensionally stable because of the width thereof and because of the material thereof, so that they form a sufficiently stable contact surface for the surface to be treated. Formed-on spacer elements can optionally be provided, by which the adjacent strip portions are supported on one another in the plane parallel to the surface to be treated. In one preferred embodiment, further material recesses are located along lateral edges of the strip, so that connecting portions exist between adjacent strip portions. In this manner, adjacent strip portions are fixed relative to one another by the connecting portions. If the strip is to be shortened by tearing off along the material recesses extending over the width of the strip, for this purpose the corresponding strip end can be detached from the adjacent strip portions in that the end to be removed is detached from the adjacent strip section by tearing off along the lateral edge. Through the material recesses extending along lateral edges can be formed in the above-described manner as material weakenings or as continuous openings.

In one expedient embodiment, the electrode arrangement can have a rectangular footprint overall, wherein the strip is formed in one piece from angled linear strip portions. In particular in this embodiment, it is expedient if a material connection detachable by material recesses exists between adjacent strip portions.

As soon as the electrode arrangement has the size of the bearing surface adapted for the application, the cover element is arranged over the free end of the strip to cover the at least one conductor extending in the end surface of the strip in an insulating manner. In one embodiment, the cover element is a contact element for supplying at least one voltage to the at least one conductor.

If the electrode arrangement has two or more conductors, all conductors can be supplied with the same voltage, for example, a high voltage. In this case, the multiple conductors jointly form an electrode, wherein the surface to be treated functions as the counter electrode if it is sufficiently conductive and is located at a sufficiently conductive ground.

It is furthermore possible to supply voltage signals which are phase-shifted in relation to one another to two conductors in such a way that the conductors are each supplied with different polarities of the voltage. In this case, a double voltage difference exists between the conductors, which facilitates the plasma formation. The surface to be treated can also function in this case as a—possibly somewhat floating—neutral electrode or ground electrode.

In another embodiment, the two conductors of the electrode arrangement can be used as electrode and counter electrode, so that a surface plasma results on the bottom side of the electrode arrangement. Such an arrangement is only reasonably usable for a surface treatment of the body provided with the surface to be treated, however. A deeper treatment, for example, of a wound area not only located on the skin surface of a body, is significantly improved by the use of the body as a counter electrode.

The supplied voltage can be an externally generated high voltage, which is required for the plasma formation. However, it is also possible to provide the electrode arrangement with a separate high-voltage step, which generates the high voltage required for the plasma generation from a supplied (harmless or at least less harmful) voltage.

It is even possible to provide the electrode arrangement with an installed battery arrangement and a separate high-voltage step, so that the plasma generation, for example, for a wound treatment, is possible fully autonomously without externally supplied voltage. In this case, the cover element connects at least two conductors and a sensor, for example, an impedance sensor, detects the connection of the conductors for the purpose of switching on the high-voltage step. The conductors connected by the cover element can be conductors which conduct the high voltage when it is ensured that non-high-voltage-proof components are overloaded. Alternatively, the two conductors can also be separate conductors, which do not conduct the high voltage, but rather are solely used for the impedance measurement and possibly a low voltage supply. It is ensured by the detection of the cover element that high voltage is not generated if the conductors discharging into the end surface of the strip are not covered in an electrically insulating manner by the cover element.

The invention will be explained in greater detail hereafter on the basis of exemplary embodiments illustrated in the drawings. In the figures.

Figure 1:
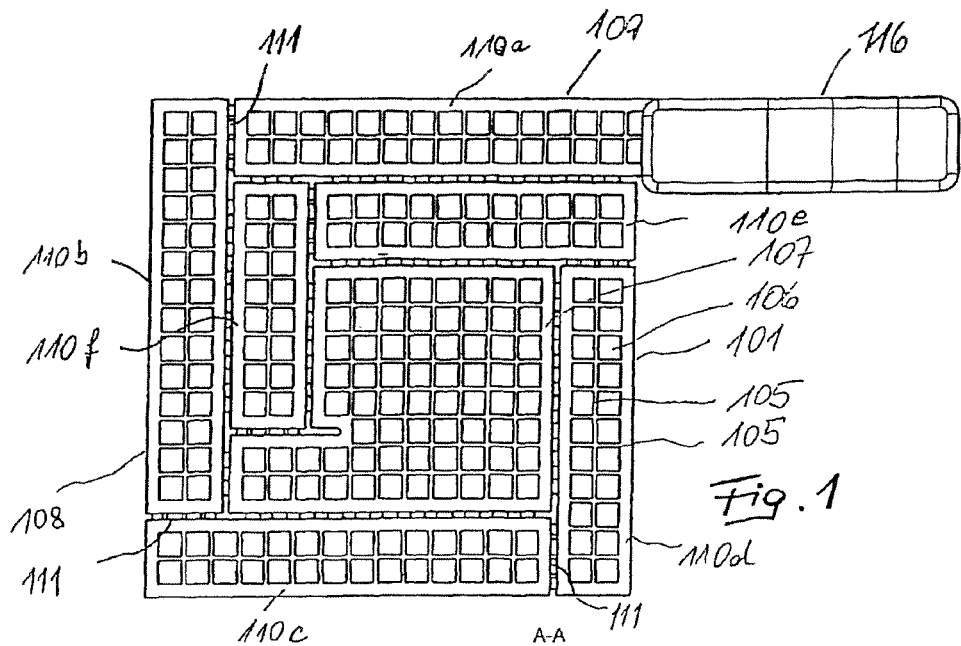
FIG. 1 shows a view of the bearing side of an electrode arrangement according to a first exemplary embodiment.

According to the first embodiment illustrated in FIGS. 1 to 4, an electrode arrangement has a planar, flexible dielectric material 101, which encloses a planar electrode 102 on all sides in an insulating manner. The dielectric material 101 forms a planar top side 103 and a planar bearing side 104, which is intended for bearing on a surface to be treated, in particular a skin surface of a human or animal. FIG. 1 shows a view of the bearing side 104. On the bearing side 104, the dielectric material is formed having a grid-like surface, on which webs 105 perpendicular to one another delimit chambers 106, in which a plasma can form by the ionization of air when the electrode arrangement rests with the bearing side 104 on a surface to be treated and the electrode 102 is supplied with a high voltage, by which the air between the dielectric material 101 and the surface to be treated is ionized, although a current flow through the dielectric material 101 is obstructed. In the first embodiment of the electrode arrangement, a high-voltage potential is supplied to the electrode 102, wherein the surface to be treated of a body acts as a counter electrode (floating ground potential).

The webs 105 are used as spacers to form an air space required for the formation of the plasma, in the form of the chambers 106 here, between the surface to be treated and the dielectric material 101 having its embedded electrode 102. Of course, the air space can also be ensured in another form, for example, by nubs or the like as spacers, wherein the air space formed in this case does not have to be laterally terminated.

The dielectric material 101 has a central region 107, in which the dielectric material is formed in one piece. An edge region 108 adjoins the central region 107 radially to the outside, in which the dielectric material is formed as a strip 109 having strip portions 110*a*, 110*b*, 110*c*, 110*d*, 110*e*, 110*f*. The strip portions are each of equal width and jointly form a strip 109 in the edge region 108, which extends in a spiral from the outer edge of the electrode arrangement to the central region 107 of the dielectric material 101. In the illustrated embodiment, the strip 109 extending in a spiral has a polygonal formation, in which the turns of the spiral strip 109 are composed of linear portions, which adjoin one another at right angles. These portions can, but do not have to, correspond to the strip portions 110*a* to 110*f*. The strip portions 110*a* to 110*f* abut one another and each have material recesses 111 extending over the strip width at the joints thereof. The material recesses 111 thus extend perpendicularly in relation to the width of the strip portions 110*a* to 110*f* and form a tear line, at which, for example, the outer strip portion 110*a* can be detached from the strip portion 110*b* by tearing off. In the same manner, it is possible to detach the strip portion 110*b* from the strip portion 110*c*, the strip portion 110*c* from the strip portion 110*d*, etc., and the radial innermost strip portion 110*f* from the central region 107 by tearing off.

Figure 4:
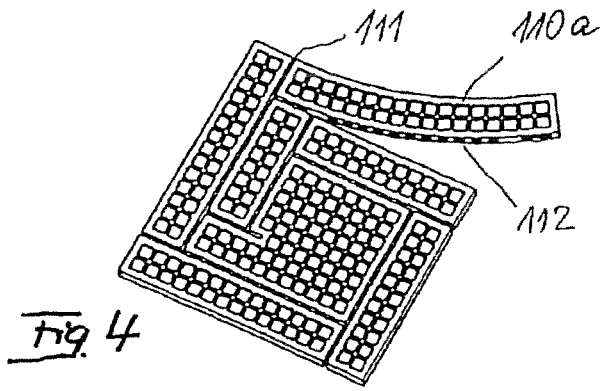
FIG. 4 shows a schematic illustration of the detaching of a strip portion to reduce the size of the contact surface of the electrode arrangement according to FIG. 1.
Figure 5:
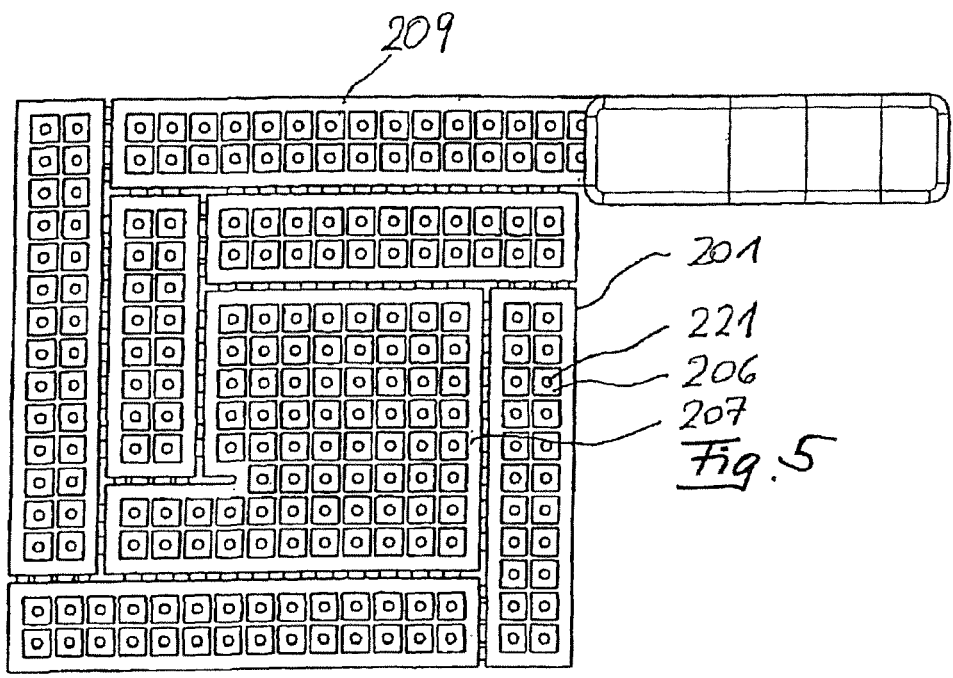
FIG. 5 shows a view from below of an electrode arrangement according to a second embodiment.
Figure 6:
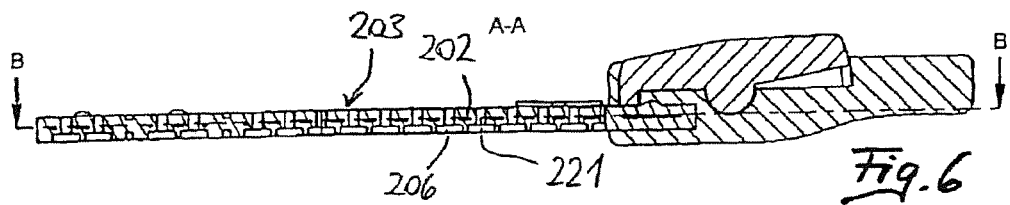
FIG. 6 shows a section through the electrode arrangement according to FIG. 5 along line A-A in FIG. 7.
Figure 7:
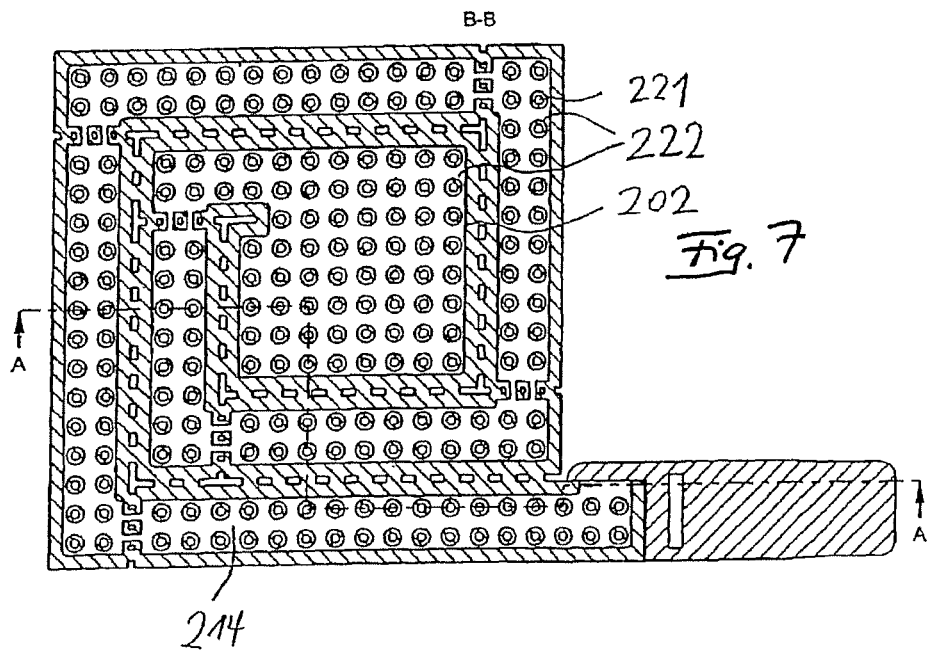
FIG. 7 shows a sectional illustration of the electrode arrangement according to FIG. 5 along line B-B in FIG. 6.
Figure 8:
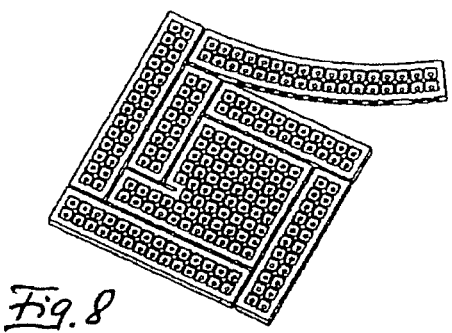
FIG. 8 shows a schematic illustration of the removal of a strip portion to reduce the size of the contact surface of the electrode arrangement according to FIG. 5.
Figure 9:
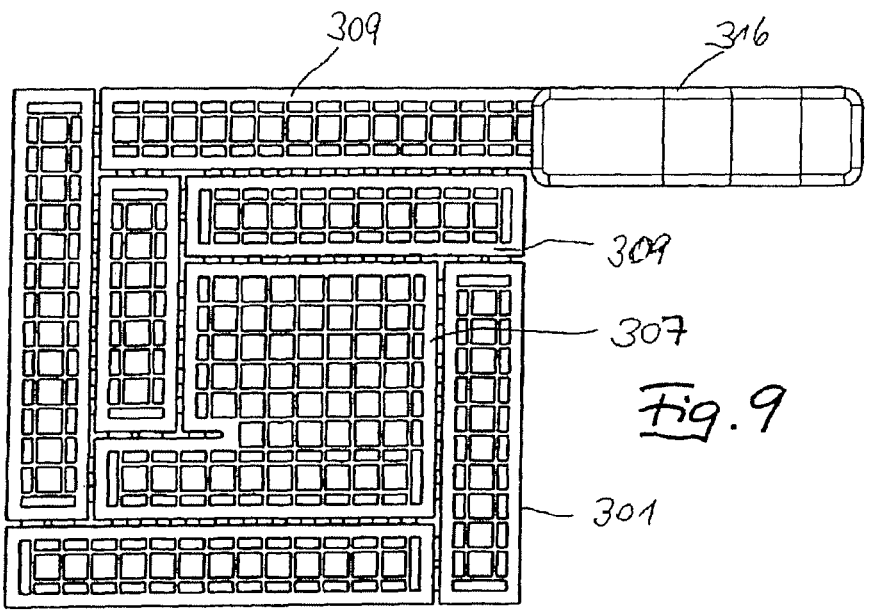
FIG. 9 shows a view from below of an electrode arrangement according to a third embodiment.
Figure 10:
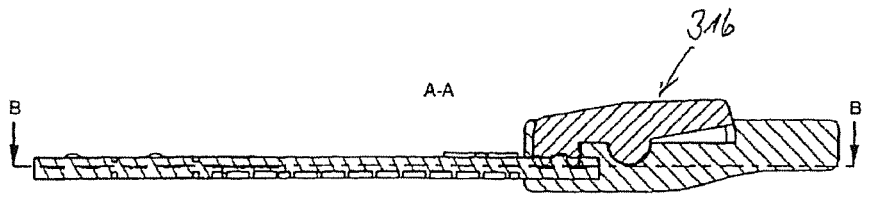
FIG. 10 shows a section through the electrode arrangement according to FIG. 9 along line A-A in FIG. 11.
Figure 11:
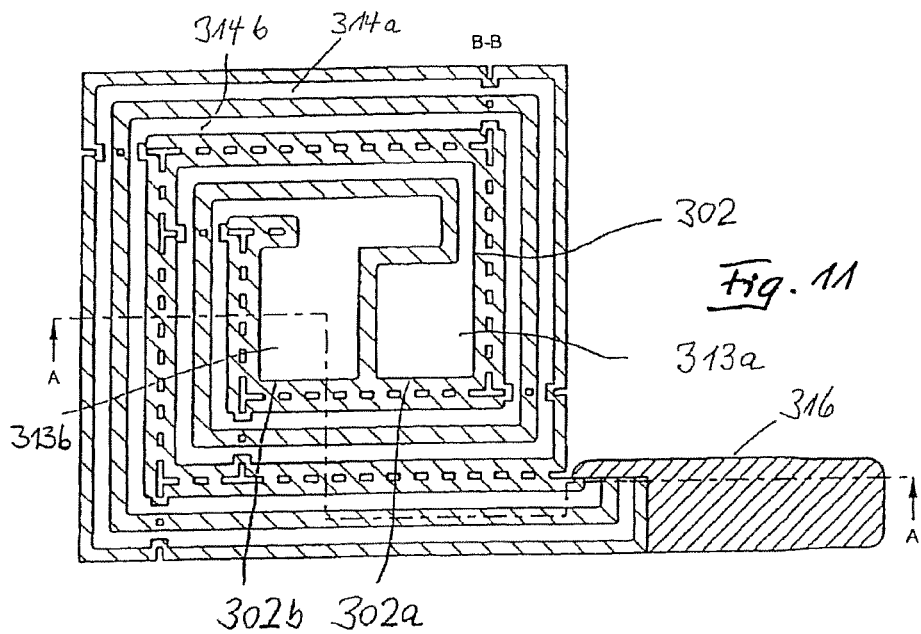
FIG. 11 shows a sectional illustration of the electrode arrangement according to FIG. 9 along line B-B in FIG. 10.
Figure 12:
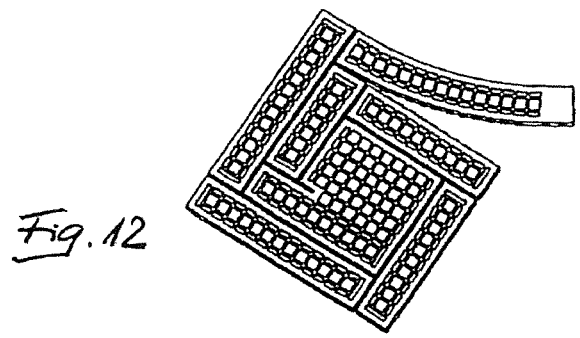
FIG. 12 shows a schematic illustration of the removal of a strip portion to reduce the size of the contact surface of the electrode arrangement according to FIG. 9.
Figure 13:
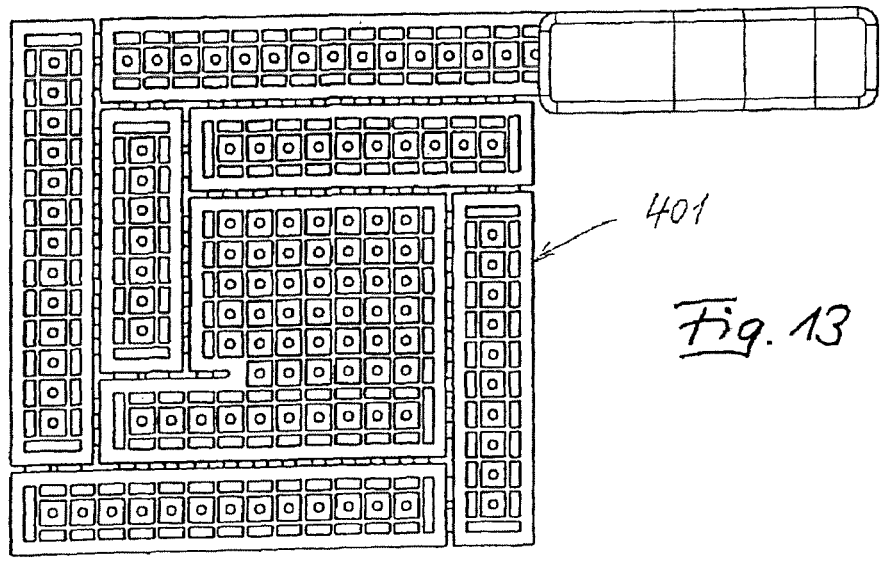
FIG. 13 shows a view from below of an electrode arrangement according to a fourth embodiment.
Figure 14:
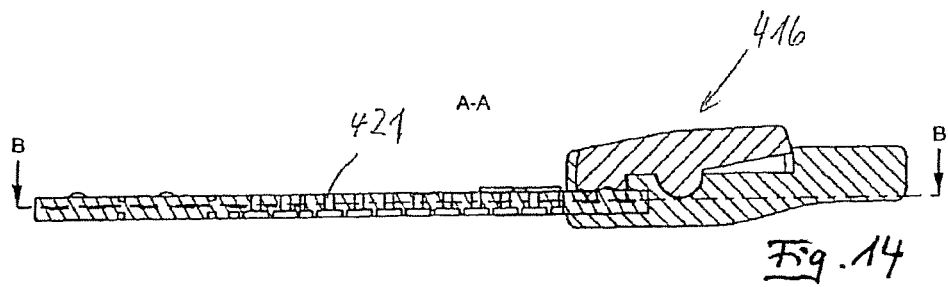
FIG. 14 shows a section through the electrode arrangement according to FIG. 13 along line A-A in FIG. 15.
Figure 15:
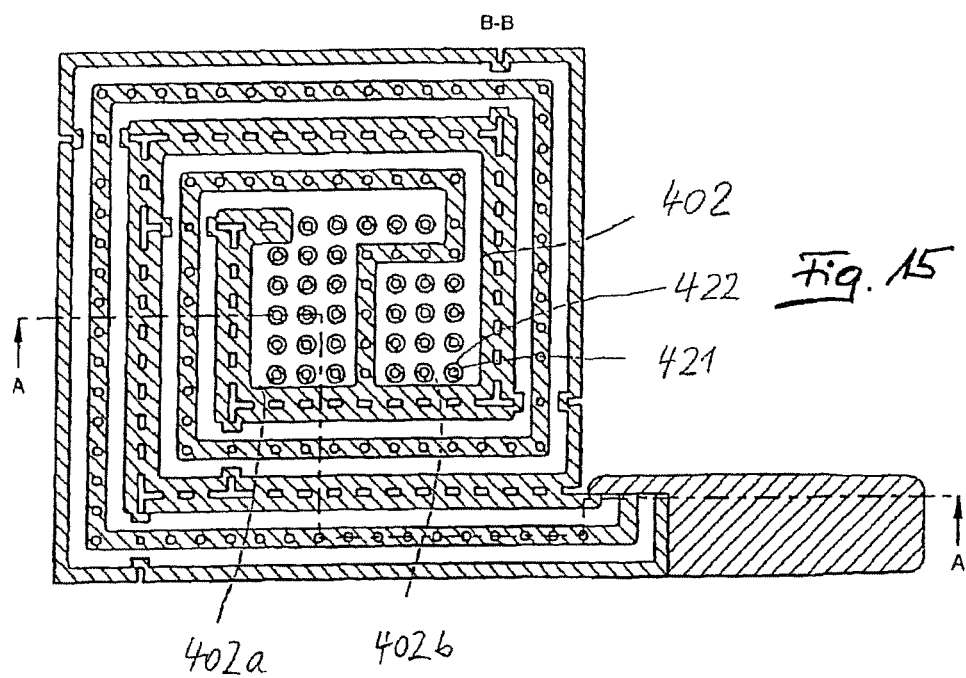
FIG. 15 shows a sectional illustration of the electrode arrangement according to FIG. 13 along line B-B in FIG. 14.
Figure 16:
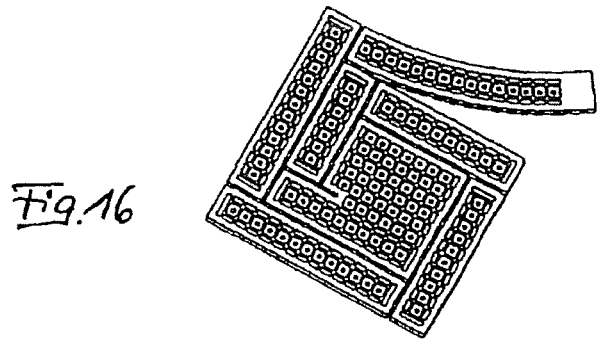
FIG. 16 shows a schematic illustration of the detaching of a strip portion to reduce the size of the contact surface of the electrode arrangement according to FIG. 13.
Figure 17:
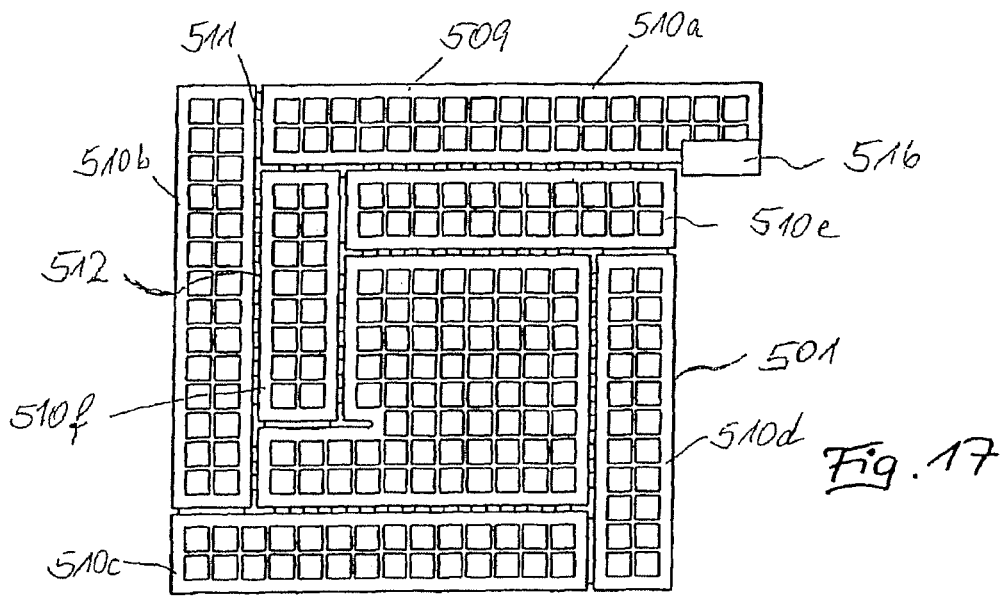
FIG. 17 shows a view from below of an electrode arrangement according to a fifth embodiment.

To enhance the stability, the strip portions 110*a* to 110*f* are connected in the illustrated embodiment to the strip portions adjacent radially inward or to the central region 107, respectively, via material recesses 112 extending in the longitudinal direction of the strip portions 110*a* to 110*f*. As FIG. 4 shows, the radial outer strip portion 110*a* can thus, for example, be detached along the material recesses 112 over its length from the remainder of the dielectric material 101 and can then be torn off along the material recesses 111 extending over the width of the strip 109, whereby the contact surface of the dielectric material may be reduced in size. For a further reduction in size, the strip portion 110*b* could be detached in a corresponding manner from the remainder of the dielectric material along the material recesses 112 and possibly torn off at the material recesses 111. In this manner, a step-by-step reduction of the contact surface of the dielectric material 101 down to at minimum the area of the central region 107 is possible. If such a strong reduction in size of the contact surface is to be performed, of course, it is not necessary to detach each of the strip portions 110*a* to 110*e* along the material recesses 111, because then detaching the last strip portion 110*f* from the central region 107 of the dielectric material is sufficient.

Figure 2:
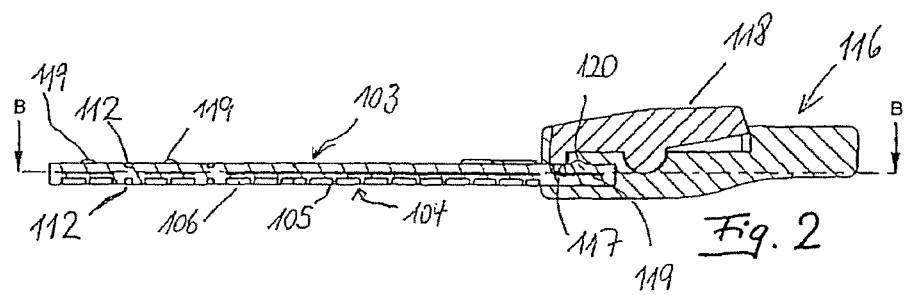
FIG. 2 shows a section through the electrode arrangement according to FIG. 1 along line A-A from FIG. 3.

FIG. 2 illustrates that the material recesses 112 only effectuate material weakenings and do not form continuous openings. The material recesses 111 are preferably formed in the same manner.

Figure 3:
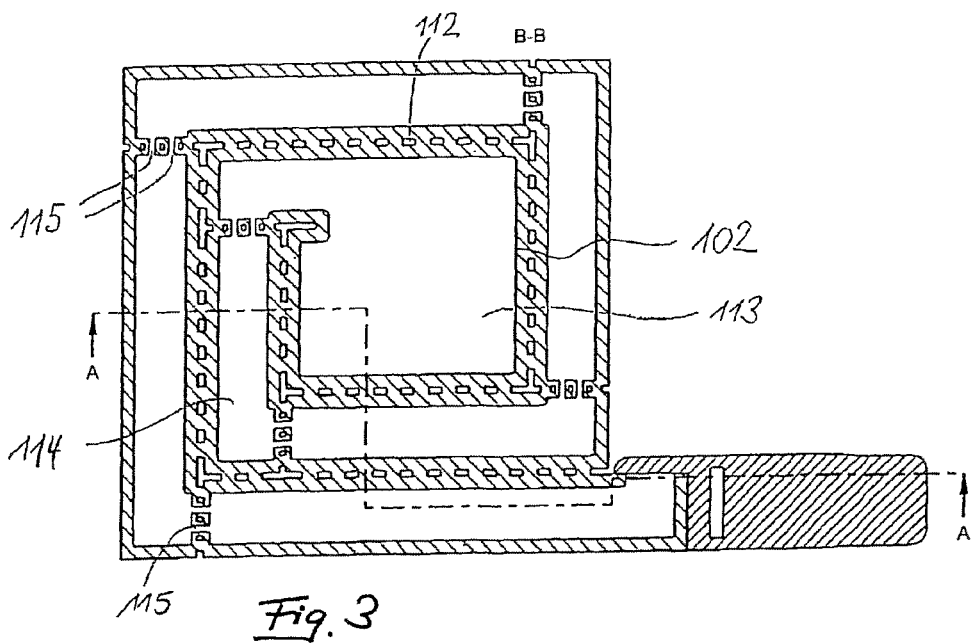
FIG. 3 shows a sectional illustration of the electrode arrangement according to FIG. 1 along line B-B in FIG. 2.

The course of the electrode 102 may be seen from FIG. 3, because the electrode is shown in a top view of the top side 103. The electrode 102 forms a corresponding central region 113, from which it extends as strip-shaped conductor 114 in spiral portions corresponding to the strip portions 110*a* to 110*f* of the dielectric material 101. In the region of the material recesses 111, i.e., in the region of the possible detachment points of the strip portions 110*a* to 110*f*, the strip-shaped conductor 114 forms narrow connecting webs 115, which also facilitate detaching the electrode 102 over the width of the strip-shaped conductor 114 and in addition ensure that material of the electrode 102 does not extend below the material recesses 111, which would only still be covered by a small dielectric material layer in the region of the material recess 111.

The material recesses 112 formed on the longitudinal edges of the strip portions 110*a* to 110*f* are recognizably located in a region in which the strip-shaped conductor 114 does not extend, so that the material regions having the material recesses 112 form intermediate spaces between the turns of the strip-shaped conductor 114.

In the illustrated embodiment, the strip portions 110*a* to 110*f* of the dielectric material 101 and the strip-shaped conductor 114 of the electrode 102 form approximately 1½ turns around the central region 107 of the dielectric material. In this manner, a substantial variation of the size of the contact surface of the electrode arrangement may be implemented. Of course, more or fewer turns may be implemented as needed, which are detachable via the material recesses 111 and possibly 112.

In particular after at least one strip portion 110*a* to 110*f* is torn off, the strip-shaped conductor 114 discharges into an end edge of the remaining strip portion 110*b* to 110*f* resulting due to the tearing off. A cover element 116 is then applied to the end of the outermost strip portion 110*b* to 110*f* or of the central region 107, respectively, remaining after the detaching, which covers the end surface having the discharging strip-shaped conductor 114 in an electrically insulating manner. In the illustrated embodiment, the cover element 116 is provided with cutting contacts 117, which are located on an actuating rocker 118 of the cover element 116 and can be pressed through the dielectric material onto the strip-shaped conductor 114 of the electrode 102, in order, for example, to transmit an externally generated high voltage to the electrode 102 by means of a cable (not shown) connected to the cover element 116. This contacting technology is known in EP 2 723 447 B1, with the result that a detailed explanation can be omitted here.

In the illustrated embodiment, the cover element 116 is to be applied in extension of the longitudinal direction of the strip 109 of the dielectric material 101, so that the strip-shaped conductor 114 of the electrode 102 discharging into the end surface can be securely covered by the cover element. Since contacting in a position of the cover element 116 rotated by 90° would also be conceivable, beads 119 extending over the width of the strip 109 are provided on the top side 103, each arranged directly behind the material recesses 111, which beads correspond to a groove 120 extending over the width of the cover element 116, so that the cover element 116 can only be applied in the correct position and the actuating rocker 118 can be actuated to contact the electrode 102. The beads 119 thus form a twist lock with the groove 120.

The second embodiment illustrated in FIGS. 5 to 8 corresponds in its construction to the first embodiment according to FIGS. 1 to 4 with the single difference that passage openings 221, which extend through the dielectric material 201 up to its top side, are provided in the bottoms of the chamber 206 terminated on top. In particular a wound secretion can be aspirated through these passage openings 221 if the electrode arrangement is formed and/or used as a wound bandage. In order that direct contact between a conductive liquid and the electrode 202 is not possible in the region of the passage openings 221, the electrodes are provided with passage holes 222, which are aligned with the passage openings 221 of the dielectric material 201 but are formed larger, so that the passage openings 221 form a passage channel having continuous dielectric walls, which also cover the electrode 202 in an insulating manner in the region of the passage openings.

The remaining construction of the second embodiment corresponds completely to the first embodiment, so that the contact surface may be reduced in size in the same manner. The passage openings 221 and the passage holes 222 of the electrode 202 are also located in the strip 209 of the dielectric material 201 and also in the strip-shaped conductor 214 of the electrode 202.

The third embodiment illustrated in FIGS. 9 to 12 corresponds to the first embodiment with the difference that the electrode 302 is formed from two partial electrodes 302a and 302b. Two central regions of the electrode 302 are thus embedded in the central region 307 of the dielectric material 301. Strip-shaped conductors 314a, 314b, which extend adjacent to one another, are insulated from one another in the turns of the strip 309 of the dielectric material 301, and which extend adjacent to one another, abut one another at the two central regions 313a and 313b of the partial electrodes 302a, 302b.

In this embodiment, the two partial electrodes 302a, 302b can interact with the surface to be treated as the counter electrode (ground electrode), by both partial electrodes 302a, 302b being supplied with the same AC high voltage. It is furthermore possible that the two partial electrodes 302a, 302b are each supplied with the high voltage via the cover element 316, but in counter phase, so that a differential voltage having twice the voltage difference of the respective peak voltages exists between the partial electrodes 302a, 302b. In a further variant of this embodiment, the two partial electrodes 302a, 302b are supplied as electrode and counter electrode, so that a surface plasma forms between the partial electrodes 302a, 302b, which can be used for superficial treatment of the surface to be treated. In this case, the surface to be treated and/or the body thereof does not function primarily as the counter electrode, since the two partial electrodes 302a and 302b form the voltage-conducting electrode and the counter electrode lying at ground.

In the fourth embodiment illustrated in FIGS. 13 to 16, the electrode 402 is again formed by two partial electrodes 402a, 402b, which extend in the same manner as in the third embodiment. In addition, however, similarly to the second embodiment of FIGS. 5 to 8, passage openings 421 are provided in the dielectric material 401 and passage holes 422 are provided in the partial electrodes 402a, 402b, respectively. This embodiment is therefore also particularly suitable as a wound bandage, but also for supplying fluid for assisting the surface treatment, which can also be wound healing. In particular, skincare substances can also be supplied through the passage openings 421 to the skin surface to be treated.

A fifth embodiment is shown in FIGS. 17 to 20, in which the bearing side 504 of the dielectric material 501 is formed in the same manner as in the first embodiment of FIG. 1. The dielectric material 501 also has a strip 509 having material recesses 511 and 512 here, by which the strip portions can be detached to reduce in size the contact surface of the bearing side 504. As explained in yet greater detail hereafter, the respective resulting free end of the strip 509 is covered by a cover element 516, via which energy supply does not take place in this embodiment. The cover element 516 firstly solely has the task of covering in an insulating manner the free edges possibly resulting upon the detachment of strip portions 510a to 510f of the electrode 502 embedded in the dielectric material 501.

Figure 19:
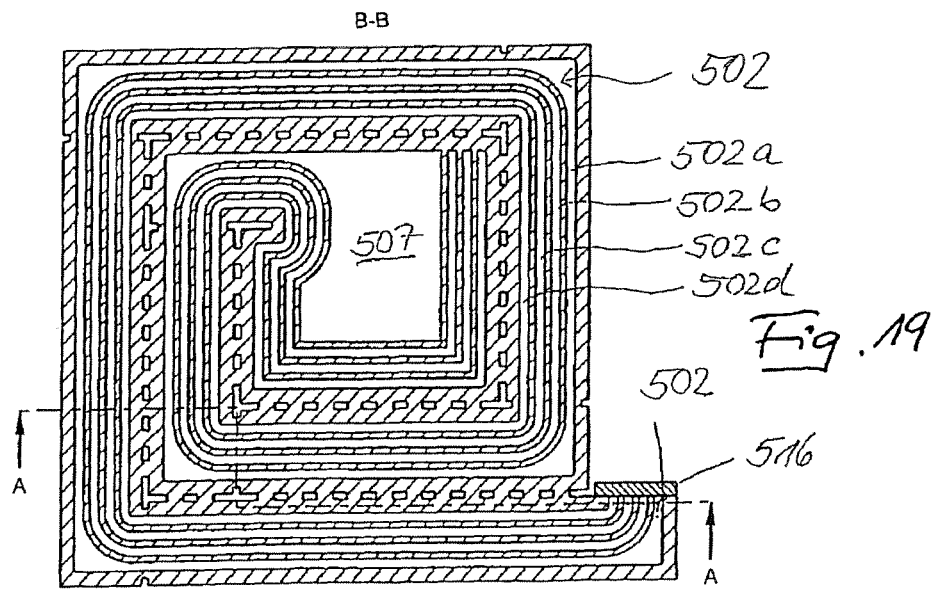
FIG. 19 shows a sectional illustration of the electrode arrangement according to FIG. 17 along line B-B in FIG. 18.

FIG. 19 shows the course of the electrode 502, which can be formed having conductors 502a, 502b, 502c, 502d extending parallel to one another.

Figure 18:
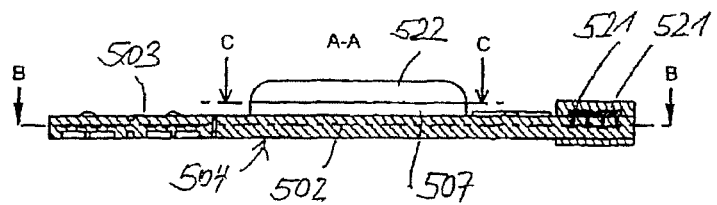
FIG. 18 shows a section through the electrode arrangement according to FIG. 17 along line A-A in FIG. 19.

As FIG. 18 illustrates, the four conductors 502a, 502b, 502c, 502d discharging into an end surface of the dielectric material 501 are not only covered by the cover element 516, but rather also connected to one another, for example, in pairs, by contact elements 521. The connection of at least two of the conductors 502a, 502b, 502c, 502d can be detected to establish the presence of the properly insulating cover element 516.

The electrode 502 can be formed by all four conductors 502a, 502b, 502c, 502d. However, it is also possible, for example, to use two of the four conductors 502a, 502b, 502c, 502d not as the electrode 502, but rather solely as a detection circuit for the presence of the cover element 516.

FIG. 18 shows that the dielectric material 501 has a type of housing structure 522 in the central region 507, which can be connected as an insulating cover element to the dielectric material 501 by adhesive bonding or welding or can be produced in one piece with the dielectric material 501.

Figure 20:
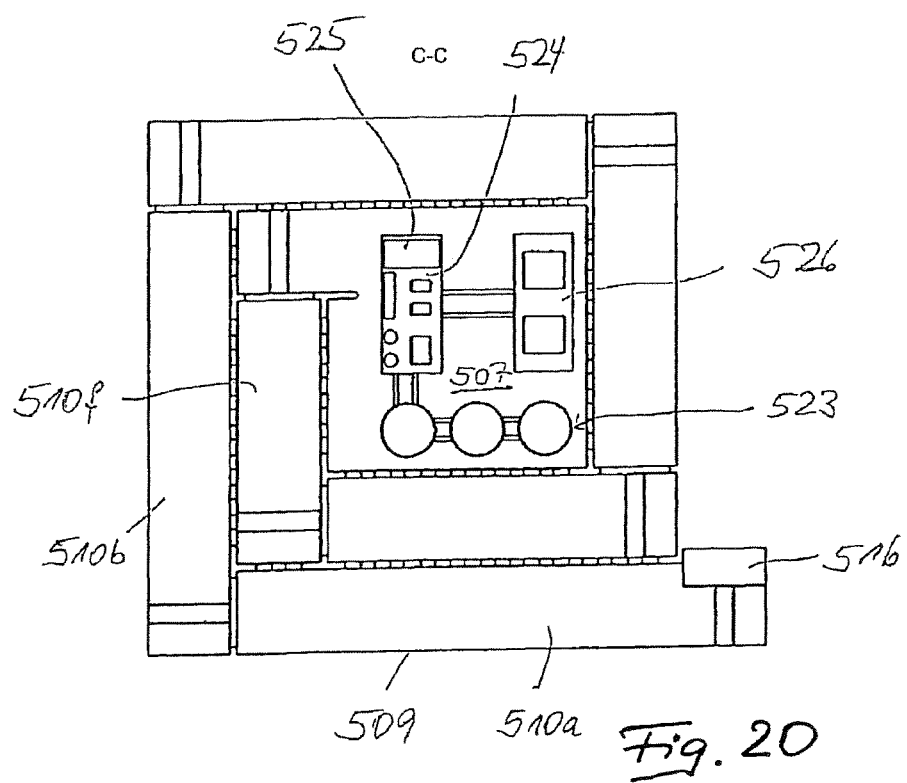
FIG. 20 shows a section through the electrode arrangement according to FIG. 17 along line C-C in FIG. 18.

FIG. 20 illustrates that the fifth embodiment in the housing structure 522 has electrical components, by way of which the electrode arrangement manages without an external electrical power supply. A battery arrangement 523, a control circuit 524 having a microcontroller 525, and a high-voltage step 526 for generating high-voltage AC voltage signals for supplying the electrode 502 are located in the housing structure 522. In the illustrated exemplary embodiment, two of the conductors 502a, 502b, 502c, 502d can function as two partial electrodes, which can be activated in the same manner as explained on the basis of the third and fourth embodiments. In particular, counter-phase AC voltage pulses can be applied to the conductors used as partial electrodes, to thus generate a particularly effective plasma field on the bearing side 504. This effect can also be amplified if all four conductors 502a, 502b, 502c, 502d are interconnected in pairs to form two partial electrodes, wherein the conductors 502a and 502c are actuated as one partial electrode and the conductors 502b and 502d are actuated as the other partial electrode.

The controller 524 has the function of only enabling the generation of the high voltage in the high-voltage step 526 when the presence of the cover element 516 has been detected. Otherwise, the conductors 502a, 502b, 502c, 502d discharging into the end surface of the strip 509 could already conduct a high voltage and could be touched directly. This is prevented by the safety circuit having the cover element 516.

FIG. 20 solely shows a top view of the top side 503 of the electrode arrangement according to the fifth embodiment outside the central region 507 having the electrical components.

The invention claimed is:

1. A planar flexible electrode arrangement for a dielectric barrier plasma discharge, comprising:
at least one planar electrode configured to receive an applied high voltage potential, wherein said at least one planar electrode is embedded in a planar dielectric material having a shape forming a top side and a bearing side and comprising a central region and an edge region, the shape further comprising a strip that extends from an end region in the edge region and, at least in the edge region, is wound in a spiral forming a wound strip that extends to an end surface, and wherein the at least one planar electrode comprises at least one planar electrical conductor which extends in a longitudinal direction of the wound strip to an end surface of the strip enclosed by the planar dielectric material of the wound strip; and a cover element comprising an electrically insulating structure which electrically insulates the end surface of the wound strip, wherein the wound strip is configured with material recesses in an arrangement forming tear-off lines that extend over the width of the wound strip and defining predetermined lengths of the wound strip as strip portions, and wherein the material recesses have a configuration that provides both the dielectric material and the at least one planar electrical conductor as manually tearable along the tear line, over the width of the wound strip.

2. The planar flexible electrode arrangement as claim in claim 1, wherein the at least one planar electrical conductor comprises a combination of a plastic with conductive additives.

3. The planar flexible electrode arrangement as claimed in claim 2, wherein the plastic of the at least one planar electrical conductor comprises a dielectric material that corresponds to the dielectric material of the at least one planar electrode.

4. The planar flexible electrode arrangement as claimed in claim 3, wherein both the plastic with the conductive additives and the dielectric material of the at least one planar electrode comprise a silicone.

5. The planar flexible electrode arrangement as claimed in claim 1, wherein the at least one planar electrical conductor extends in portions of the width of the wound strip which are not interrupted by the material recesses.

6. The planar flexible electrode arrangement as claimed in claim 1, wherein at least two of the strip portions of the wound strip are arranged as radially adjacent strip portions, having respective lateral edges that are mutually adjacent in a radial direction relative to the central region, the respective lateral edges that are mutually adjacent in the radial direction are connected by connecting portions of the dielectric material, the electrode arrangement further comprises additional material recesses, located along the connecting portions of the dielectric material, between the respective lateral edges of the radially adjacent strip portions.

7. The planar flexible electrode arrangement as claimed in claim 1, wherein the at least one planar electrical conductor is formed in the wound strip and has a conductor width, and the conductor width is reduced in a region of the material recesses.

8. The planar flexible electrode arrangement as claimed in claim 1, wherein the at least one planar electrical conductor has perforation passages, the perforation passages being aligned with the material recesses of the wound strip in the direction of the width of the wound strip, and the perforation passages have a configuration providing for manual tearing off of the at least one planar electrical conductor along the tear-off line formed by the material recesses of the wound strip.

9. The planar flexible electrode arrangement as claimed in claim 1, wherein the electrode arrangement has a rectangular footprint, and wherein the wound strip comprises linear strip portions in an arrangement forming angled abutments with one another.

10. The planar flexible electrode arrangement as claimed in claim 1, wherein the cover element comprises a contact element configured to receive at least one voltage and to supply the received at least one voltage to the at least one planar electrical conductor.

11. The planar flexible electrode arrangement as claimed in claim 1, wherein the at least one planar electrical conductor is among a plurality of planar electrical conductors that are embedded in and extend in the longitudinal direction of the wound strip, and the cover element connects to at least two of the planar electrical conductors, and the electrode arrangement further comprises:
a battery arrangement installed in the electrode arrangement;
a separate high-voltage step which is connected to the battery arrangement; and
a sensor that is configured to detect the connection of the at least two planar electrical conductors and, responsive to detecting the connection, to switch on the high-voltage step.

\* \* \* \* \*